United States Patent [19]
Armstrong

[11] 3,983,392
[45] Sept. 28, 1976

[54] METHOD AND APPARATUS FOR MEASURING INCOMBUSTIBLE CONTENT OF COAL MINE DUST USING GAMMA-RAY BACKSCATTER

[75] Inventor: Frederick E. Armstrong, Copan, Okla.

[73] Assignee: The United States of America as represented by the United States Energy Research and Development Administration, Washington, D.C.

[22] Filed: Feb. 14, 1975

[21] Appl. No.: 550,099

[52] U.S. Cl. .................................. 250/272; 250/273
[51] Int. Cl.² ..................... G01N 23/20; G21K 1/00
[58] Field of Search .......... 250/272, 273, 274, 308, 250/358, 306

[56] References Cited
UNITED STATES PATENTS

| | | | |
|---|---|---|---|
| 3,448,264 | 6/1969 | Rhodes | 250/280 |
| 3,693,079 | 9/1972 | Walker | 250/358 |
| 3,735,126 | 5/1973 | Casper | 250/273 |
| 3,736,426 | 5/1973 | Anderson et al. | 250/273 |
| 3,749,910 | 7/1973 | Carr-Brion et al. | 250/273 |
| 3,840,746 | 10/1974 | Kehler | 250/360 |
| 3,868,509 | 2/1975 | Fasching et al. | 250/358 |

*Primary Examiner*—Alfred E. Smith
*Assistant Examiner*—David K. Moore
*Attorney, Agent, or Firm*—Dean E. Carlson

[57] ABSTRACT

Method and apparatus for measuring incombustible content of particulate material, particularly coal mine dust, includes placing a sample of the particulate material in a container to define a pair of angularly oriented surfaces of the sample, directing an incident gamma-ray beam from a radiation source at one surface of the sample and detecting gamma-ray backscatter from the other surface of the sample with a radiation detector having an output operating a display to indicate incombustible content of the sample. The positioning of the source and detector along different surfaces of the sample permits the depth of the scattering volume defined by intersection of the incident beam and a detection cone from the detector to be selected such that variations in scattered radiation produced by variations in density of the sample are compensated by variations in the attenuation of the incident beam and the gamma-ray backscatter.

17 Claims, 5 Drawing Figures

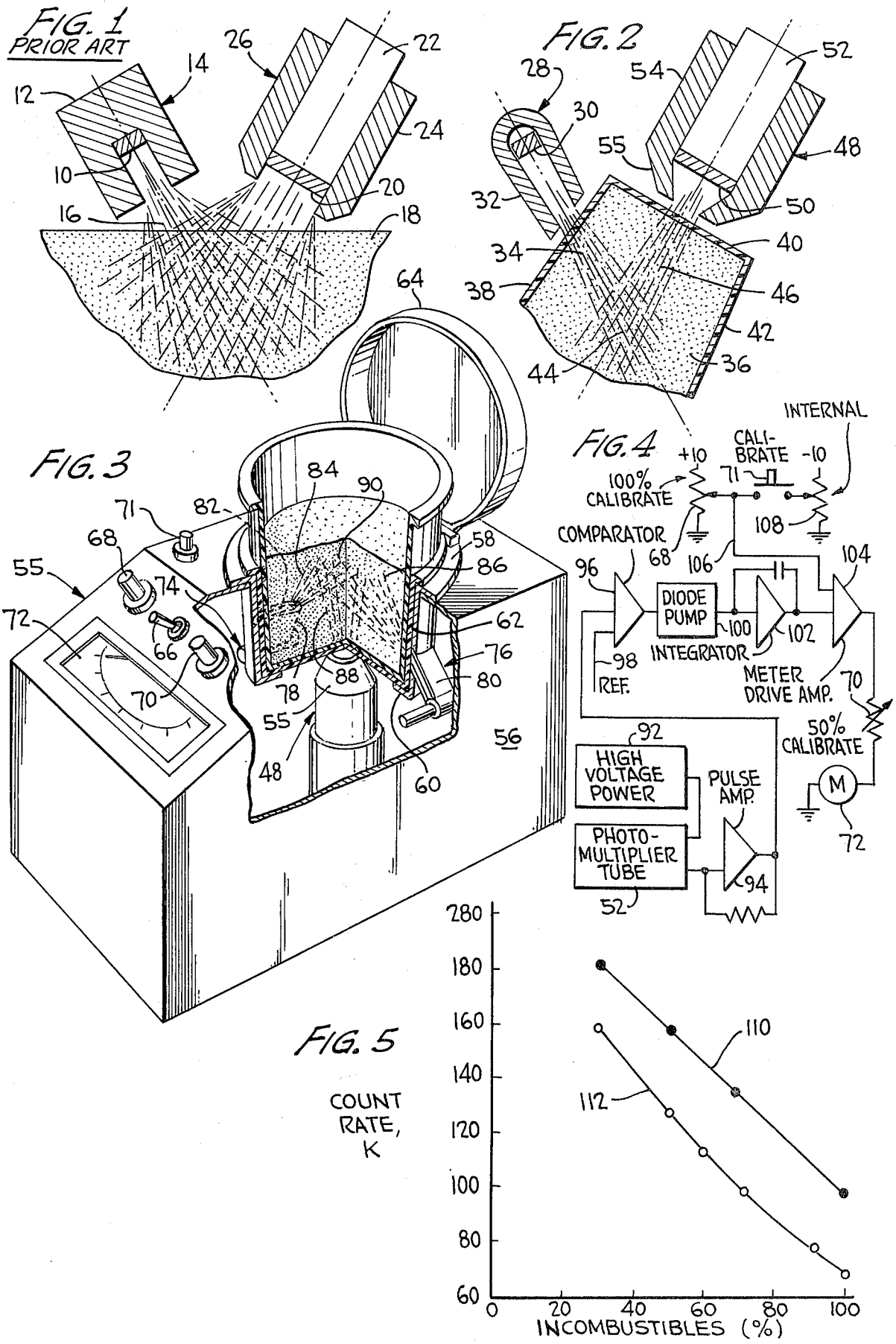

METHOD AND APPARATUS FOR MEASURING INCOMBUSTIBLE CONTENT OF COAL MINE DUST USING GAMMA-RAY BACKSCATTER

BACKGROUND OF THE INVENTION

1. Field of the Invention

The present invention pertains to radiation backscatter measurement of particulate material and, more particularly, to method and apparatus using a gamma-ray backscatter technique for determining incombustible content of coal dust and rock dust mixtures in coal mines.

2. Discussion of the Prior Art

The major source of energy in disastrous coal mine explosions is the explosive combustion of coal dust. Such explosions usually are initiated by the explosion of a relatively small amount of methane which blows coal dust lying on the floor or walls of the mine into the air and simultaneously ignites it. The resulting secondary explosion blows still more coal dust into the air and ignites it, and the explosion is thus propagated throughout the mine or until an area is reached where insufficient fuel is available to maintain combustion.

One way that such explosion propagation can be prevented is by mixing rock dust, such as limestone or dolomite, with the coal dust in sufficient quantity to produce a mixture containing 65% or more of inert, incombustible material. The Coal Mine Safety Act of 1969 requires all mine operators to maintain such a minimum incombustible material concentration in all dust found underground undergound coal mines at distances greater than 40 feet from a working face.

It becomes necessary, therefore, to provide a method for determining the amount of incombustible content in coal mine dust, both from the operator's standpoint of knowing when sufficient rock dust has been applied and from the mine inspector's viewpoint during a mine inspection. At present, two methods, volumetry and, much less commonly, a chemical or ashing method, are used to measure the amount of incombustibles in coal mine dust. The more commonly used method, volumetry, is a very simple liquid-displacement technique for determining the specific gravity of a 20-gram sample of the mixture of coal and rock dust. Although reasonably accurate, this method has the disadvantages of being time consuming and requiring a considerable amount of equipment and reagent; and, furthermore, this method has the greater disadvantage of being essentially a laboratory technique thereby requiring that samples be collected underground, packaged and transported to the mine entrance, often several miles away, for shipment to a laboratory. Obviously, a rapid, accurate, instrumental method capable of use in situ would be most desirable for determining the percentage of incombustible material in coal mine dust, not only to decrease the time required for a sample to be analyzed by an inspector, but also to permit hazardous conditions to be detected and corrected in as short a time as possible.

Experimental work with the use of gamma-ray backscatter and transmission absorption techniques for determining coal ash content has been reported by several investigators in the past. A preliminary investigation by J. W. Martin and R. F. Stewart, "Determination of Incombustible Content of Mine Dust By Nuclear Method," BuMines RI 7193, 1968, showed that, using an americium-241 source, roughly a 30% change in counting rate resulted from a 35% change in incombustible content in the range of interest, 50 to 80% total incombustible content. This measurement was performed using a flat sample surface of "infinite" thickness, about 4 inches for americium-241; however, because a sufficient sample is seldom available to provide an infinite thickness in practice, a different approach was required.

The use of scattered gamma-rays to determine shale and ash in coal has been studied in the past with the result that it was determined that the use of low energy (below 100 kev) gamma-rays was necessary to obtain sufficient difference in scattered characteristics of carbon and those of heavier elements to accomplish the desired purpose. Thulium 170 with an 85 kev gamma-ray was used for an irradiation source in these studies; and, as reported by L. Hardt, "A Rapid Method For Determining The Ash Content of Coal By Means of Low Energy Radiation," Paper B3, 4th International Coal Preparation Congress, England, published by National Coal Board, pp. 101-108, 1962, and Martin and Stewart, mentioned above, as well as others, the sample thickness was required to exceed three inches. Hardt suggested six inches and Martin and Stewart suggested four inches dependent primarily on the isotope (and consequent gamma-ray energy) employed. Accordingly, the use of a flat scattering surface imposes a minimum sample size or, in the case of in situ measurements, a minimum sample thickness and, therefore, has the disadvantage of requiring large samples or thick beds of dust.

An additional problem involved in the measurement of incombustibles content of coal mine dust is that of variation in bulk density of the sample. It has been discovered that at selected spacings of the radiation source sample and detector, a combination could be achieved at which the backscatter measurement was uneffected by changes in bulk density, as exemplified by U.S. Pat. No. 3,505,520 to Stewart et al, but the use of such a combination has the disadvantage that it is effective for only a single particular incombustible composition and introduces error for other compositions.

While the above described prior art systems have been found satisfactory for laboratory studies, considerable modifications thereof would be required to produce a satisfactory field instrument for in situ use. The basic problem to be overcome stems from the fact that although the source-detector separation technique for bulk density compensation is operable for a given sample composition, it actually exaggerates the problem with different compositions.

SUMMARY OF THE INVENTION

Accordingly, it is a primary object of the present invention to overcome the above discussed disadvantages of the prior art by providing method and apparatus for accurately measuring incombustible content of coal mine dust using a gamma-ray backscatter technique wherein the measurement can be accomplished with a field instrument for use in situ.

Another object of the present invention is to direct a tightly collimated incident radiation beam into a sample container at a point slightly offset above an edge of the bottom of the container and detect radiation backscatter from the bottom surface of the sample whereby compensation is provided for bulk density variations while permitting good accuracy with samples as small as 100 grams.

A further object of the present invention is to hold a sample of particulate material in a container to define angularly oriented surfaces of the sample, direct a low energy incident radiation beam at one sample surface and detect radiation backscatter from the other sample surface, the scattering volume defined by the intersection of the incident beam and a detection cone being positioned at a depth within the sample such that variations in scattered radiation caused by density variations of the sample are compensated by attenuation of the incident beam and the backscattered radiation.

Yet an additional object of the present invention is to provide an instrument for in situ measurement of incombustible content of coal mine dust including a container support recessed in a top wall of a housing for the instrument to receive a sample of coal mine dust and position the sample between a pair of line sources of gamma-ray incident beams with a gamma-ray detector disposed under the sample to detect gamma-ray backscatter and operate a display on the housing to indicate the incombustible content of the sample.

The present invention is generally characterized in apparatus for measuring the incombustible content of particulate material using a radiation backscatter technique including a container for holding a sample of the particulate material having first and second angularly oriented walls defining first and second angularly oriented surfaces of the sample, a radiation source for producing a low energy incident radiation beam directed through the first wall of the container at the first surface of the sample, and a radiation detector disposed adjacent the second wall of the container for detecting backscattered radiation from the second surface of the sample whereby variations in scattered radiation caused by variations in density of the sample are compensated by variations in attenuation of the incident radiation beam and the backscattered radiation.

The present invention is further characterized in a method of measuring incombustible content of coal mine dust using a gamma-ray backscatter technique including the steps of filling a container having first and second angularly oriented walls with a coal mine dust sample to define first and second angularly oriented surfaces for the sample, directing a low energy incident gamma-ray beam at the first surface of the sample, and detecting gamma-ray backscatter from the second surface of the sample whereby variations in scattered radiation caused by variations in density of the sample are compensated by attenuation of the incident gamma-ray beam and the gamma-ray backscatter.

Another object of the present invention is to reduce the effect of moisture content in a sample being measured by a gamma-ray backscatter technique by utilizing two line sources of radiation on opposite sides of a sample container.

Some of the advantages of the present invention over the prior art are that compensation is provided for bulk density variations and moisture content of particulate material being measured, an instrument incorporating the method and apparatus of the present invention can be produced for in situ use and measurements can be quickly and accurately obtained for various incombustible compositions therby facilitating inspection and reducing the time required to detect and correct hazardous conditions.

Other objects and advantages of the present invention will become apparent from the following description of the preferred embodiment taken in conjunction with the accompanying drawings.

BRIEF DESCRIPTION OF THE DRAWINGS

FIG. 1 is a diagrammatic illustration of a prior art technique of gamma-ray backscatter measurement.

FIG. 2 is a diagrammatic illustration of a technique of gamma-ray backscatter measurement in accordance with the present invention.

FIG. 3 is a perspective with parts broken away of an instrument for determining incombustible content in accordance with the present invention.

FIG. 4 is a schematic diagram of a counting rate meter circuit for the instrument of FIG. 3.

FIG. 5 is a graph illustrating the relationship of count rate to incombustible content for different rock dusts measured with the instrument of FIG. 3.

DESCRIPTION OF THE PREFERRED EMBODIMENT

In general, gamma-ray backscatter measurement is performed by directing a collimated beam of gamma-rays toward a flat surface of a material to be analyzed and detecting the gamma-rays that are scattered and deflected backward and upward from the sample surface. The amount of detected reflected gamma-rays depends upon the kind of material in the surface, the density of the material, the energy of the incident gamma-rays and the efficiency of the detector. Several kinds of interactions take place between the incident gamma-ray beam and the material that it penetrates during the scattering process with low (below 100 kev) gamma-ray energies, the predominant loss taking place through photoelectric absorption which is the primary effect with which the present invention is concerned. The scattering process itself involves both coherent scattering, in which the energy of the scattered gamma-ray is unchanged, and Compoton scattering, in which the energy of the scattered gamma-ray is degraded during the process. The present invention is primarily concerned with Compton scattering.

The photoelectric absroption process takes place when an incident gamma-ray is absorbed by an orbital electron of a material being axamined. Thus, it can be seen that the amount of the material which, in turn, is dependent upon the atomic number of the elements making up the material. The orbital electron is ejected when an incident gamma-ray is absorbed and carries with it the energy of the incident gamma-ray minus the binding energy of the electron. The cross-section, or probability that this reaction will take place, is thus dependent upon the binding energy of the orbital electron and is greatest for those electrons with the highest binding energy, the K electrons. The binding energy increases rapidly with atomic number; and, accordingly, the probability becomes much larger for those elements with higher atomic numbers. Although the exact relationship of cross-section to nuclear charge and gamma-ray energy is very complex, in the lower gamma-ray energy range, below 100 kev, the cross-section varies approximately as the third power of the gamma-ray energy and the fourth power of the atomic weight.

Coal mine dust is a mixture of coal (which contains incombustible material in the form of ash), rock dust, usually limestone or calcium carbonate, and a few percent of moisture. The average density of coal mine dust of 65% incombustible content is about 1.0. The density of solid coal is about 1.35 and that of limestone about 2.7. By simple calculation, it can be seen that coal mine dust is composed of about 45% solids and 55% void space. The main atomic numbers for coal and rock dust are 6 and 12, respectively; and, thus, the electron density of rock dust is approximately twice that of coal dust. Use of these data permits the calculation of both gamma-ray attenuation and backscatter characteristics for mixtures of rock dust and coal dust. It has been found that in the desired range of 50-100% incombustible content, a variation of nearly 2:1 in backscatter gamma-ray intensity takes place when the energy of the incident gamma-ray beam is of the order of 60 kev.

A conventional configuration employed in prior art gamma-ray backscatter measuring systems is shown in FIG. 1 wherein a source of gamma-rays 10 is housed in a shield 12 to form a collimated radiation source 14. A gamma-ray incident beam 16 emanates from the radiation source 14 and strikes a particulate material 18 being examined, the material 18 having a flat surface. A portion of the incident beam is scattered backward and upward to strike a detector crystal 20 attached to a photomultiplier tube 22 and housed in a shield 24 to form a detector 26. With this configuration gamma-rays are scattered from the surface of the sample 18 as well as from a volume within the sample that is dependent upon the density of the sample. That is, as sample density increases, the volume of maximum scatter moves toward the surface because a greater number of gamma-rays are attenuated both entering and after scattering by the increased density. The result is a net increase in backscattered gamma-rays and by moving the radiation source 14 and the detector 26 away from the sample 18, a decrease in backscatter takes place. At a particular distance for any given sample composition, a condition exists where changes in density over a limited range do not cause similar changes in total backscatter flux. This distance is known as the bulk density minimum distance. Because of the dependence upon composition, this configuration is useful only where accuracy is required for only a single particular composition.

Apparatus according to the present invention is illustrated in FIG. 2 wherein a radiation source assembly 28 includes a source of radiation 30 disposed in a housing shield 32 providing a tightly collimated incident beam of gamma-rays 34 which strike a sample of particulate material 36 at a side surface 38 offset from an end surface 40. The sample 36 is held in a container 42 which has angularly oriented side and bottom walls for defining an angularly orientation between side surface 38 and end surface 40. The incident radiation beam 34 penetrates the sample 36 to some depth and is scattered from a volume 44 defined by the intersection of the radiation beam and a detection cone 46 subtended by a detector assembly 48 formed of a sodium iodide crystal detector 50 coupled to a photomultiplier tube 52 and contained in a collimating housing shield 54 having a conical end 55. The depth of the subtended scattering volume 44 is chosen such that variations in the amount of scattered radiation produced by variations in density are exactly compensated by variations in attenuation of the incident beam and the backscattered radiation beam produced by variations in density. This effect is made possible by the fact that no direct scattering from the surface or at shallow depths in the sample 38 can reach the dectector crystal 50 because of the specific configuration of the sample and due to the very tightly collimated incident beam of radiation as well as the tight collimation of the detector assembly 48.

To take a measurement, an operator in a coal mine collects a sample of between 125 and 200 grams of sieved coal/rock dust mixture to fill the container 42, and the container is then positioned adjacent the source and detector assemblies such that the angular orientation of the side and end surfaces of the sample coupled with the positioning of the source and detector assemblies will compensate for bulk density variations. The container 42 may, for example, be a polystyrene drinking cup. The thin wall of such cups (about 0.09 gram/centimeter$^2$) produces a minimal effect upon the scatter measurement, and the relatively precise nature of injection molding for producing such drinking cups insures reproducibility from cup to cup.

An instrument 55 according to the present invention utilizing the basic conept of FIG. 2 is illustrated in FIG. 3 and includes a housing 56 having a cylindrical container support recessed in a top wall thereof and formed of a cup-like member 58 having an inwardly extending bottom flange 60 and a cup-like liner 62 disposed within the member 58 to prevent contamination of the member by coal mine dust or other material commonly found in coal mines. A lid 64 hingedly connected with the container support to cover the top opening thereof when the instrument is not in use. Disposed on the face of the housing 56 are an on/off switch 66, a 100% calibrate potentiometer 68, a 50% calibrate potentiometer 70, a calibration switch 71, and an analog display meter 72, and within the housing are suitable high and low voltage supplies and a counting rate meter circuit for driving meter 72. The voltage supply and counting circuitry are conventional; and, while a specific counting rate meter circuit is described below and shown in FIG. 4, other circuitry could be used with the present invention.

The detector assembly 48 for the instrument of FIG. 3 is the same as that described with respect to FIG. 2 and is mounted in housing 56 such that the conical end 55 of the shield is centered below the container support 58. A pair of radiation source assemblies 74 and 76 are disposed on diametrically opposite sides of the container support and include sources of radiation, such as americium 241, disposed in housing shields 78 and 80, respectively. Both of the shields 78 and 80 have a flattened configuration to define a slot opening 82 in the ends thereof, and the ends extend through the member 58 to abut the liner 62. The source assemblies 74 and 76, thus, define a pair of line sources of incident radiation on opposite sides of the container support to overcome the problems associated with the use of a single source, as will be discussed hereinafter. The source assemblies 74 and 76 are angularly oriented to direct incident beams 84 and 86 centrally and upwardly into the sample to intersect with each other and with the detection cone 88 subtended by the detector assembly 48 to define a scattering volume 90 at a depth within the sample such that any variations is scattered radiation caused by any variations in density of the sample will be compensated by variations in attenuation of the incident and backscattered radiation beams.

One example of a counting rate meter circuit that can be used with the present invention is shown in FIG. 4 wherein the photomultiplier tube 52 of the detector assembly 48 receives power from a high voltage power supply 92 and supplies negative pulses corresponding to radiation detected by crystal detector 50 to an operational amplifier 94. The output of amplifier 94 is supplied to a comparator 96 which also receives a reference voltage input from 98 corresponding to radiation of 40 kev such that output pulses from comparator 96 represent only radiation over 40 kev. The output from the comparator 96 is supplied through a diode pump 100, a low-offset-current integrator 102 having a 20-second time constant with only 0.2uF in the feedback circuit, an amplifier 104 and 50% calibrate potentiometer 70 to meter 72. Amplifier 104 receives a calibration input on a lead 106 which is connected with a tap of potentiometer 68 and through calibration switch 71 with a tap of an internal potentiometer 108. Power for the instrument is supplied by two 12-volt, nickel-cadmium batteries, and a voltage regulator reduces the 24-volt supply voltage to 12 volts for supply to a DC to DC converter forming the high voltage power supply 92 and for supply to Zener diodes providing plus and minus 10 volts to potentiometers 68 and 108, respectively.

Of course, any suitable circuitry can be used to provide power and operate the meter 72; however, the described circuit has the advantage that drift is minimal.

Calibration of the instrument is accomplished by placing a 100-percent incombustible rock dust sample in container 42 and placing the container in measuring position in support 58 in the instrument. The instrument is then turned on via switch 66; and, after one minute (three time constants) the 100-percent calibrate potentiometer is adjusted to set the meter deflection to the 100-percent mark which corresponds with zero deflection of the meter. The calibrate switch 71 is then pushed, and the 50-percent potentiometer is adjusted to set the meter at the 50-percent mark.

In operation, once the instrument is calibrated, a sample of coal mine dust to be analyzed is obtained and screened to contain particles no larger than those which will pass through a 20-mesh screen. The screened sample is then placed in a polystyrene drinking cup 42, and the cup is placed in the container support 58 in the instrument 55. The switch 66 is then pushed, and the percent incombustible material of the sample can be read from movement of the needle of meter 72. The angular orientation of the source assemblies 74 and 76 is preset for the angular configuration of the side and end walls of the cup 42 in order to obtain compensation for density variations; and, due to the manner of production of polystyrene cups, such cups can be disposed of after a measurement with a new cup used for the next measurement.

While design factors will vary with applications of the present invention, it is desired for coal mine dust measurements to have a maximum analysis time of one minute and a maximum permissible error of 1%. Accordingly, as in an example, a total of not less than 10,000 counts per determination would be required. Using a total americium-241 source activity of 30 millicuries and the geometry above described, a counting rate ranging from 70,000 to 160,000 counts per minute was achieved over the range of interest, 50 to 100 percent incombustible content, with a 5-mm thick, 1-inch diameter sodium-iodide crystal detector. The variation in count rate for limestone and dolomite rock dusts is shown in FIG. 5. It should be noted that the dolomite curve 110 is linear and that, while the limestone is nonlinear over the whole range, it is relatively straight over the 50 to 100 percent range.

The two-radiation source configuration of FIG. 3 has an advantage over the single radiation source configuration of FIG. 2 in that with the apparatus of FIG. 2, the effect of moisture content in the sample is not compensated while the use of a pair of oppositely disposed line radiation sources overcomes this problem, it being noted that moisture content is not significant until levels of 6 to 8% are reached. Additionally, with the apparatus of FIG. 2, nonhomogeneous packing in the sample container 42 can cause an error of as much as 7 or 8% when the sample container is removed and replaced in a slightly different position relative to the source assembly 28; however, the use of the two line radiation sources renders the read-out of the instrument of FIG. 3 independent of angular orientation of the sample container. Of course, a ring radiation source surrounding the sample container could be used in accordance with the present invention; however, for economic reasons, the use of two diametrically opposed radiation sources is preferred.

From the above, it will be appreciated that by directing a tightly collimated incident radiation beam at a surface of a sample different from a surface of the sample from which backscatter radiation is received in a tightly collimated detector in accordance with the present invention variations in density of the sample will not produce inaccuracies in measurement. The angular orientation of the radiation sources depends upon the angular relation of the two surfaces of the sample such that the detection cone subtended by the detector intersects the incident radiation beams to define a scattering volume at a proper depth to provide compensation for variations in scattered radiation with variations in density.

The radiation source material used in the radiation source assemblies 74 and 76 is a radiosotope producing monoenergetic low energy gamma-rays, that is gamma-rays with energies below 100 kev. For example, the source material could be Am-241 (39 and 60 kev) or I-125 (27 and 35 kev) or any other suitable conventional source of low energy gamma-ray radiation. The material of detector 50 can be thin crystals of sodium iodide or anthracene, with a diameter of 1 inch and a thickness of from 1mm to 6mm. The detector crystal operates, as is well known, by interacting with incident gamma photons to produce light having an intensity proportional to the energy of the absorbed photons, and the photomultiplier tube is responsive to the light pulses from the crystal detector to produce current pulses supplied to the counting rate meter circuit. The meter 72 has been shown as providing an analog display or read-out; however, a digital read-out could be provided if desired.

Inasmuch as the present invention is subject to many variations, changes and modifications in detail, it is intended that all subject matter mentioned above or shown in the accompanying drawings be interpreted as illustrative and not in a limiting sense.

What is claimed is:

1. Apparatus for measuring the incombustible content of particulate material using a radiation backscatter technique comprising
container means for holding a sample of the particulate material, said container means having first and second angularly oriented walls defining first and second angularly oriented surfaces of the sample; first and second radiation source assembly means disposed on opposite sides of said container for producing low energy incident beams through said first wall of said container means at the first surface of the sample; and radiation detector means disposed adjacent said second wall of said container means for detecting backscattered radiation from the second surface of the sample whereby variations in scattered radiation caused by variations in density of the sample are compensated by variations in attenuation of said incident radiation beam and said backscattered radiation.

2. Apparatus as recited in claim 1 wherein said radiation source means produces a gamma-ray incident beam and said radiation detector means detects gamma-ray backscatter.

3. Apparatus as recited in claim 1 wherein said radiation detector means defines a subtending detection cone intersecting said incident radiation beams at said scattering volume whereby error from moisture content and non-homogeneous packing of the sample is minimized.

4. Apparatus as recited in claim 3 wherein each of said source assemblies has a housing shield producing a line incident radiation beam.

5. Apparatus as recited in claim 4 wherein each of said incident radiation beams is tightly collimated and said detection cone is tightly collimiated.

6. Apparatus as recited in claim 1 wherein said incident radiation beam is tightly collimated, and said radiation detector means has a tightly collimated detection cone.

7. Apparatus as recited in claim 6 wherein said radiation detector means includes a housing shield having a conical end subtending said tightly collimated detection cone.

8. Apparatus as recited in claim 1 wherein said container means has a cup-like configuration with a side wall defining said first wall and a bottom defining said second wall.

9. Apparatus as recited in claim 8 wherein said container means is a polystyrene cup.

10. An instrument for measuring incombustible content of coal mine dust in situ using a gamma-ray backscatter technique comprising an instrument housing having a top wall with container support means recessed therein having angularly oriented bottom and side wall means for receiving a container holding a sample of the coal mine dust;

gamma-ray source means arranged in said housing on opposite sides of said side wall means for producing tightly collimiated incident gamma-ray beams intersecting within said side wall means;

gamma-ray detector means arranged in said housing below said bottom wall means subtending a tightly collimated detection cone intersecting said incident gamma-ray beams within said bottom and side wall means to define a scattering volume in the coal mine dust sample, said gamma-ray detector means detecting gamma-ray backscatter and supplying an output corresponding thereto; and circuit and display means receiving said output from said gamma-ray detector means and providing a display of the incombustible content in the coal mine dust sample, the instrument of said gamma-ray source means and said gamma-ray detector means being such that said scattering volume is located at a depth within the coal mine dust sample to permit variations in scattered radiation caused by variations in sample density to be compensated by variations in attenuation of said incident gamma-ray beams and said gamma-ray backscatter.

11. An instrument as recited in claim 10 wherein said container support means includes a cup-like outer support and an inner liner.

12. An instrument as recited in claim 11 wherein said circuit and display means includes an analog meter.

13. An instrument as recited in claim 10 wherein gamma-ray source means includes a pair of source assemblies producing line incident gamma-ray beams.

14. An instrument as recited in claim 10 wherein said container support means has a cup-like configuration and further comprising a polystyrene cup for holding a coal mine dust sample and adapted to be received in said container support means.

15. A method of measuring incombustible content of coal mine dust using a gamma-ray backscatter technique comprising the steps of filling a container having first and second angularly oriented walls with a coal mine dust sample to define first and second angularly oriented surfaces for the sample;

directing from oppositely disposed radiation sources low energy incident gama ray beams at said sample and detecting gamma-ray backscatter from said second surface of said sample whereby variations in scattered radiation caused by variations in density of the sample are compensated by attenuation of the incident gamma-ray beam and the gamma-ray backscatter.

16. A method as recited in claim 15 wherein said directing step including directing a plurality of low energy, incident gamma-ray beams at the first surface of the sample from various positions around the container.

17. A method as recited in claim 16 and further comprising the step of screening the coal mine dust sample before filling the container.

* * * * *